(12) United States Patent
Haun et al.

(10) Patent No.: US 7,832,253 B1
(45) Date of Patent: Nov. 16, 2010

(54) PORTABLE WEATHER RESISTANT GAS CHROMATOGRAPH SYSTEM

(75) Inventors: Darrell N. Haun, Sugar Land, TX (US); Donald N. Haun, Stafford, TX (US)

(73) Assignee: Solarcraft, Inc., Stafford, TX (US)

( * ) Notice: Subject to any disclaimer, the term of this patent is extended or adjusted under 35 U.S.C. 154(b) by 92 days.

(21) Appl. No.: 12/397,010

(22) Filed: Mar. 3, 2009

(51) Int. Cl.
*G01N 30/00* (2006.01)

(52) U.S. Cl. .............. 73/23.22; 73/23.35; 73/23.41; 73/23.42; 73/431; 95/82; 96/101; 96/102; 96/106; 422/89; 422/104

(58) Field of Classification Search ............ 73/23.22, 73/23.35, 23.41, 23.42, 431; 95/82; 96/101, 96/102, 106
See application file for complete search history.

(56) References Cited

U.S. PATENT DOCUMENTS

| | | | | |
|---|---|---|---|---|
| 3,060,301 A | * | 10/1962 | Rondle | 219/400 |
| 4,553,985 A | * | 11/1985 | Dahlgren et al. | 95/26 |
| 5,123,276 A | * | 6/1992 | Hartman et al. | 73/23.41 |
| 5,361,626 A | * | 11/1994 | Colligan et al. | 73/40.7 |
| 5,559,283 A | * | 9/1996 | Kaji et al. | 73/61.56 |
| 5,591,406 A | * | 1/1997 | Hirai et al. | 422/80 |
| 5,711,916 A | * | 1/1998 | Riggs et al. | 422/83 |
| 2003/0085714 A1 | * | 5/2003 | Keyes et al. | 324/464 |
| 2010/0032600 A1 | * | 2/2010 | Doe et al. | 251/129.15 |

OTHER PUBLICATIONS

Fast Online Gas Chromatograph Analysis for LPG Distillation, Yokogawa, 2007, pp. 1-3.*
Process Gas Chromatograph PGC 9000 VC, RMG Messtechnik Gmbh, Nov. 2008, pp. 1-8.*

* cited by examiner

*Primary Examiner*—Daniel S Larkin
(74) *Attorney, Agent, or Firm*—Buskop Law Group, PC; Wendy Buskop

(57) ABSTRACT

A portable weather resistant gas chromatograph system with a gas chromatograph enclosure having a body and a movable door and a seal, a gas chromatograph with a frame assembly removably secured in the enclosure, a plurality of exhaust gas lines connected to the gas chromatograph, an explosion proof terminal box with circuit breakers and terminals mounted to the enclosure, a communication conduit and armored power cable between the explosion proof terminal box and the gas chromatograph, a purge gas conduit port for the gas chromatograph, a pedestal for the enclosure, and at least two lifting eyes connected to the enclosure.

19 Claims, 4 Drawing Sheets

PORTABLE WEATHER RESISTANT GAS CHROMATOGRAPH SYSTEM

FIELD

The present embodiments generally relate to a gas chromatograph system that is tough, weather resistant and liftable without deformation for use in the field, particularly in harsh environments, such as the Arctic or Saudi Arabia.

BACKGROUND

A need exists for a sturdy prefabricated enclosure to house a gas chromatograph system. Generally, in order to perform gas chromatography a facility or a building is required for housing the required equipment.

A further need exists for a portable, self contained and self powered gas chromatograph which can be delivered to remote locations within a sturdy enclosure.

A further need exists for a non-deformable portable enclosure for a gas chromatograph. Gas chromatographs require gas lines for purge gases, calibration gases, and sample gases and therefore a need exists for a portable enclosure which will not deform and stress or rupture any gas lines and their connections during transport.

The present embodiments meet these needs.

BRIEF DESCRIPTION OF THE DRAWINGS

The detailed description will be better understood in conjunction with the accompanying drawings as follows.

Figure 1:
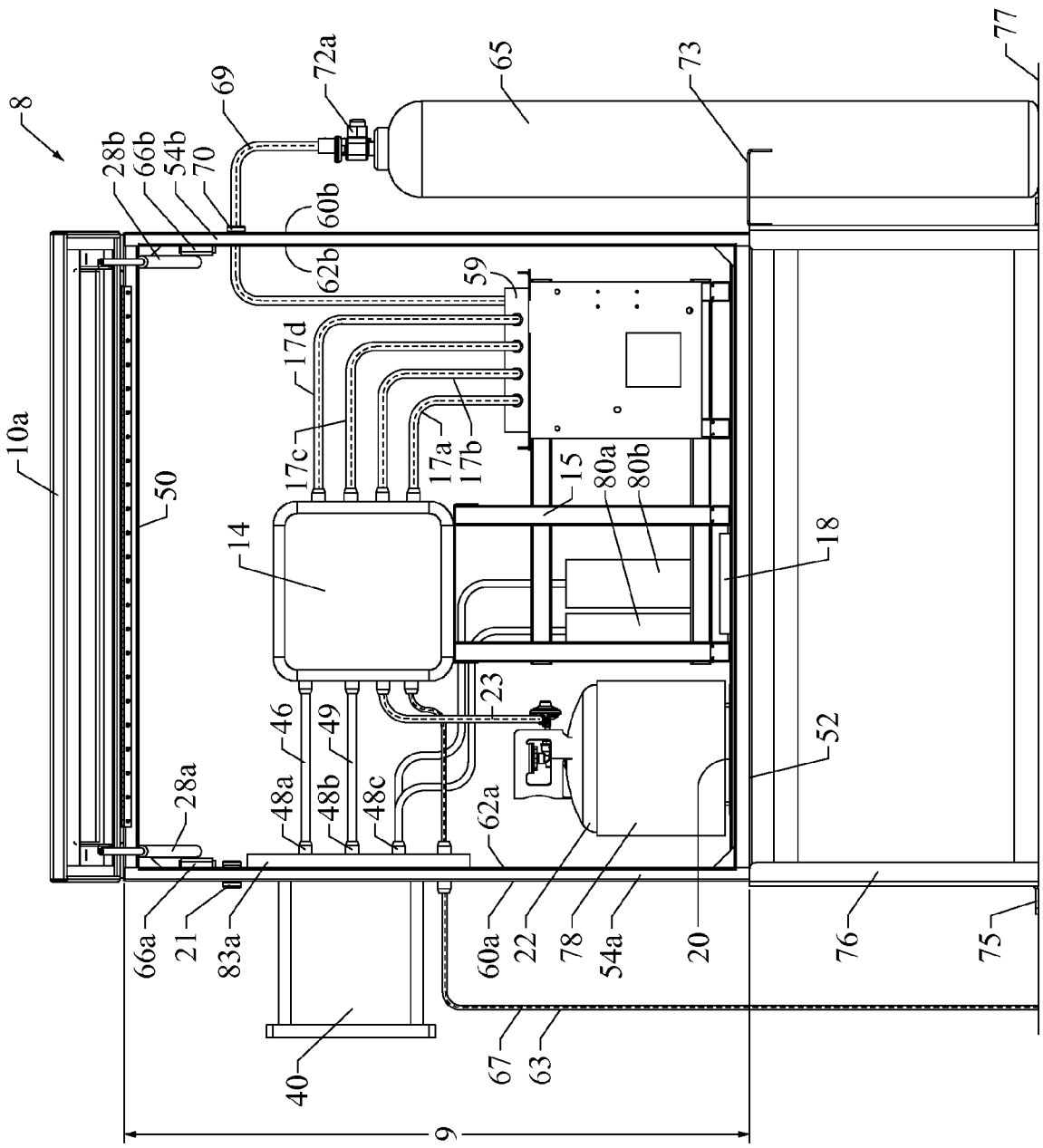
FIG. 1 illustrates a front view of an enclosure containing a gas chromatograph in accordance with one embodiment of the present invention.

The present embodiments are detailed below with reference to the listed Figures.

DETAILED DESCRIPTION OF THE EMBODIMENTS

Before explaining the present system in detail, it is to be understood that the system is not limited to the particular embodiments and that it can be practiced or carried out in various ways.

The present embodiments relate to a portable weather resistant gas chromatograph system.

The system includes a gas chromatograph enclosure which can be made from powder coated metal.

The gas chromatograph enclosure can have a body and a movable door that can be adapted to engage the body. The body can be generally a rectangular box with the movable door hinged to the body overlapping the walls of the rectangular box. The movable door can, in another embodiment be removable from the body and attachable to the body with a plurality of fasteners, such as two fasteners, for two opposing walls.

The body can be square or rectangular and have five walls each having an outer side and an inner side forming a chamber with an opening. The body can also include four sides proving openings in two opposite sides. In either embodiment, one of the walls can form a base.

The body can further be oval or circular in shape, then only two or three walls would be used with one wall being for the bottom or base.

In an embodiment, at least one movable door fastener can be used to secure each wall to the movable door.

In an embodiment the body can be about fifty-four inches high, about fifty-four inches wide, and about twenty-eight inches deep. The body can be made from a power powdered coated aluminum having a aluminum thickness of between about $1/16$ inches to about $3/8$ inches.

The movable door can be the same height and width as the body, but can have an overhanging lip of up to several inches enabling the movable door to cover the open portion of the body and cover part of any wall that forms the portions of the body engaging the movable door. The movable door can be powder coated aluminum with an aluminum thickness of about $1/16$ to about $3/8$ inches.

A seal, such as a rubber gasket, can be about two inches wide and about $1/4$ inches to about $1/2$ inches thick. The seal can be fastened to the movable door to provide a weather tight sealing engagement with the body, so that no water, steam, sand or other undesirable materials get inside the enclosure.

A gas chromatograph can be positioned within the body. An example of a gas chromatograph can be a unit available from Daniels™ of Houston, Tex. or from those made available by Fisher Scientific.

The gas chromatograph can be positioned on a frame assembly and can further be secured to the frame assembly with fasteners such as bolts. Parts of the gas chromatograph can be removed from the frame assembly for repair or replacement if needed.

The frame assembly can be constructed from a metal alloy or other rigid material. In an embodiment, the frame assembly can be contemplated to be movably secured to a support that in turn can be secured to an inside wall of the body. The support can be two parallel bars of channel steel spaced apart. The support can be made of other metals and other rigid materials for the purpose of providing additional support to the enclosure.

At least two exhaust gas lines to about four exhaust gas lines can be fluidly connected between the gas chromatograph and the body. More exhaust gas lines can be contemplated for use with this invention, for example eight exhaust lines can be used with certain embodiments of the present invention. These exhaust lines can be made from metal conduits for carrying pressurized sample gas, inert gas and pressurized purge gas. These sample lines can further be contemplated to sustain pressures between about 0 PSI to about 1000 PSI and can withstand exposure to corrosive and harsh gases without degradation for several years. The exhaust gas can include a sample gas, a purge gas, an inert gas and another gas. A manifold can be used in fluid communication between the plurality of exhaust gas lines for venting exhaust gas out of the body.

An explosion proof terminal box with a height of about ten inches, a width of about ten inches and a depth of about six inches, which can be made from metal with an appropriate plate thickness, can be mounted to an outside portion of one of the walls of the body.

The explosion proof terminal box can be in communication with the gas chromatograph through the wall on which the explosion proof terminal box can be mounted.

The explosion proof terminal box can have at least one circuit breaker and can have at least two terminals, but can have between one and six circuit breakers and up to about twenty-four terminals. The explosion proof terminal box can also be lockable.

A conduit can be used to provide communication between the explosion proof terminal box and the gas chromatograph. The conduit can be insulated with a sleeve.

At least one armored power cable can provide power between the explosion proof terminal box and the gas chromatograph. This power cable can provide AC current of between about 110 volts to about 220 volts. The explosion proof terminal can receive power from a power station, a solar array, or from another power source. The circuit breaker contained within the explosion proof terminal box can serve to distribute power to each element within the body requiring power in the enclosure.

A purge gas conduit port can be placed in one of the walls of the body for accepting purge gas to be used for the gas chromatograph. The purge gas can come from a purge gas source outside of the body.

A pedestal can be used for maintaining the gas chromatograph enclosure above a surface such as the ground, in case of flooding so none of the tanks or equipment are exposed to drifting sands, flood waters or wildlife.

A first lifting eye can be riveted, welded or bolted to a first wall of the body and a second lifting eye can be similarly connected to a second wall opposite the first lifting eye. This design enables a crane, such as a pedestal crane to lift the portable weather resistant gas chromatograph system with all the equipment mounted it in without deforming the gas chromatograph enclosure. Non-deforming lifting of such heavy and calibrated equipment without damage is an amazing feat and is needed in the field.

In an embodiment, the support can be two parallel stiff non-deformable bars fixedly secured to an inner side of one of the walls. These supports can be welded, bolted or riveted on an inner side of a wall to reinforce the support of explosion proof terminal box mounting on the outer side of that same wall. The non-deformable bars can be constructed from aluminum, steel, other metals, or other rigid materials.

In another embodiment, a flange can be welded to one of the walls. The flange can encircle the walls, like a small frame assembly on top of the body. The flange can be used to support the first and second lifting eyes. The flange can also have lifting holes drilled in it for lifting of the portable weather resistant gas chromatograph system without the lifting eyes.

An embodiment contemplates that the system can include at least one heater, which can be thermostatically controlled, contained in the body. Two heaters can be used in an embodiment. The heaters can be connected to the explosion proof terminal box in order to receive the power they require to operate.

A calibration gas tank can be used in an embodiment of the system. In the calibration gas tank can be a calibration gas for calibrating the gas chromatograph. The calibration gas tank with calibration gas can be in fluid connection with the gas chromatograph.

In an embodiment, the calibration gas tank can be contained within the pedestal, while in another embodiment the calibration gas tank can be located externally to the body.

One or more tank fastening systems can be mounted to an outer side of one of the walls of the body. The tank fastening system can include a frame assembly and chain, a frame assembly and nylon strap or a hinged and locking frame assembly for holding one or more tanks of purge gas, such as helium. The tank fastening systems can secure the calibration gas tank as well.

A heating blanket can be used around the calibration gas tank. The heating blanket can receive power from the explosion proof terminal box.

Insulation, such as sheets of insulating material or coatings of insulating material can be secured or applied to the inside of each of the walls of the body. Depending on the material used, the insulation coating can range from relatively thin to about an inch thick. The overall size of the interior insulation can match the dimensions of the inner side of the walls of the body. The insulation can cover all or part of the walls, but covering at least about fifty percent can be contemplated as useful to reduce water build up inside the body.

A purge gas regulator, which can be fluidly connected between the purge gas conduit port and the purge gas source, can be used for reducing pressure of purge gas prior to flowing the purge gas to the gas chromatograph.

The conduit between the gas chromatograph and the explosion proof terminal box can be contemplated to have at least two sealing fittings in the conduit. The conduit can have a sealing fitting on the inner side of the wall through which the conduit extends and on the outer side of the wall through which the conduit extends.

One embodiment can include a foldable tray between about ten inches to about sixteen inches in length, about six inches to about ten inches in width and a thickness suitable for supporting a portable device. The foldable tray can be mounted to the frame assembly for supporting a computer, a laptop, or other computing device. The foldable tray can fold out from the frame assembly providing unique space saving.

A calibration gas frame assembly can be made of metal or another suitable material and can be dimensioned for supporting the calibration gas tank. The calibration gas tank assembly can be connected to the bottom of the body for supporting the calibration gas tank above the bottom of the body.

In an embodiment, the air around the gas chromatograph in the body can be temperature and pressure controlled using a temperature control, a pressure control or combinations thereof.

The movable door can be controlled using two pneumatic shocks. One pneumatic shock can be connected on an inner side of a first wall, and the other pneumatic shock can be connected to a second wall on the inner side opposite the first wall. Channel bars can be used to add strength to the walls and reinforce the power of the pneumatic shocks when used with the movable door. The channel bars can be welded or bolted to the walls and the shocks can be bolted or attached to the channel bar.

A thermostat can be used in the body and can be connected to one or more of the heaters and a terminal in the explosion proof junction box, for temperature regulation.

Turning now to the Figures, FIG. 1 depicts a gas chromatograph enclosure 8 including a body 9 resting on a pedestal 76. The body 9 is illustrated with a plurality of walls, including a top 50, a bottom 52 and at least two sides 54a, 54b. One of the walls 54a is illustrated with an inner side 62a and an outer side 60a and another wall 54b is illustrated on the opposite side with an inner side 62b and an outer side 60b. The bottom 52 can rest in the pedestal 76. Pedestal flanges 75 on the bottom of the pedestal 76 can provide a secure means for resting flush with a surface 77 and for fastening the pedestal 76 to the surface 77. The modular design of the gas chromatograph enclosure 8 allows a crane to move and position the system, and the pedestal flanges 75 permit securing the system at a single location.

FIG. 1 illustrates a movable door 10a in an open position providing access to the components contained within the body 9. The movable door 10a can be controlled using two pneumatic shocks 28a, 28b. One pneumatic shock 28a can be connected on an inner side 62a of a first wall 54a through a channel bracket 66a, and one pneumatic shock 28b the can be connected to a second wall 54b on the inner side 62b of the opposite wall 54b through a channel bracket 66b. In one embodiment, a single pneumatic shock or multiple pneumatic shocks can operate a movable door. The pneumatic shocks can also be mounted directly on the walls 54a, 54b.

A gas chromatograph 14 can be secured within the body 9 on a frame assembly 15. The frame assembly 15 can be connected to the bottom 52 of the body 9. The gas chromatograph 14 can be a unit available from Daniels™ of Houston, Tex. or a unit available from Fisher Scientific.

A sample gas line 63 can provide a sample gas 67 for analysis by the gas chromatograph 14. The sample gas line 63 can be connected to an external source, such as a pipe line.

A calibration gas frame assembly 20 can support a calibration gas tank 22, which can be connected to the gas chromatograph 14 for supplying calibration gas 23. The calibration gas tank 22 is illustrated with a heating blanket 78 for regulating the temperature of the calibration gas 23.

FIG. 1 also illustrates a purge gas conduit port 70, which can be placed in one of the walls 54b of the body 9 for accepting purge gas 69 to be used for the gas chromatograph 14. The purge gas 69 can come from a purge gas source 65 illustrated as a tank outside the body 9 in this Figure. A purge gas regulator 72a can be located between the purge gas source 65 and the purge gas conduit port 70 and can regulate the purge gas 69 into the body 9 and into the gas chromatograph 14.

The gas chromatograph enclosure 8 can have at least one exhaust gas line 17a, 17b, 17c, 17d, which can fluidly connect between the gas chromatograph 14 and the body. A manifold 59 can further be in fluid communication with at least one exhaust gas line 17a, 17b, 17c, 17d for venting exhaust gas from the body 9.

Figure 4:
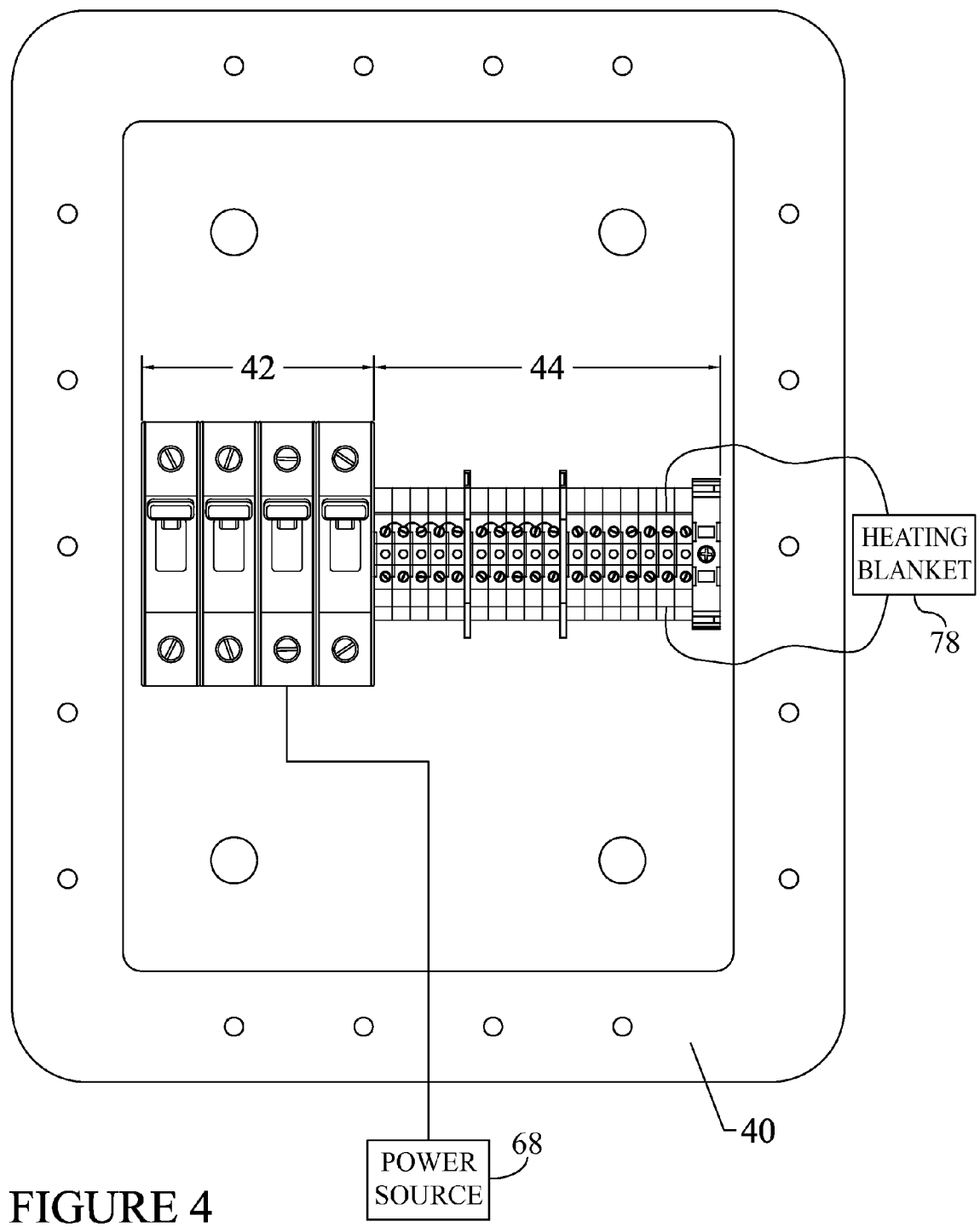
FIG. 4 illustrates a power source connected to a circuit breaker of one embodiment of the present invention.

Attached to the exterior of the body 9 can be an explosion proof terminal box 40 which can enclose terminal 44 and a circuit breaker 42 for communication with a power source 68, shown in more detail in FIG. 4.

In FIG. 1, the explosion proof terminal box 40 can communicate with the gas chromatograph 14 through a conduit 46. The conduit 46 can be connected through the wall 54a of the body 9 with sealing fitting 48a for preventing fluid and gases from passing in and out of the body 9. Additional sealing fittings 48a, 48b, 48c are also depicted in this Figure.

The conduit can be a power cable, a fiber optic cable or communication cables around a power cable, contained or not contained in a housing, such as a flexible plastic tube.

The gas chromatograph 14 can be supplied with power through an armored power cable 49, which can further be connected to the circuit breaker 42, which is shown in FIG. 4.

A parallel stiff non-deformable bar 83a is illustrated on the inner side 62a of wall 54a. While one parallel stiff non-deformable bar 83a is visible in this figure, a second parallel stiff non-deformable bar can be mounted behind the first, and a plurality of parallel stiff non-deformable bars can be mounted in a row. One or more of the parallel stiff non-deformable bars can be used as braces for mounting the explosion proof terminal box 40 on the exterior of the body 9.

Heaters 80a, 80b can provide a thermostatic control for regulating the temperature range within the body 9. Each heater 80a, 80b can receive power from the explosion proof terminal box 40. The heaters 80a, 80b can be located near the support assembly 15, but those of ordinary skill in the art can appreciated the heaters 80a, 80b can be located anywhere within the body 9.

Pressure relief valve 21 can regulate the internal pressure of the body 9 and can further provide an outlet for releasing pressure.

The exterior of the body 9 can also include a tank fastening system 73 for securing the purge gas source 65, which is illustrated as a tank to the exterior or the body 9.

A foldable tray 18 can be mounted on the bottom 52 of body 9. The foldable tray can be affixed with hinges in order to pivot between two positions. The foldable tray is shown in an fully stowed storage position, but can pivot roughly about one hundred and eighty degrees providing a flat surface for laptops or other portable devices.

Figure 2:
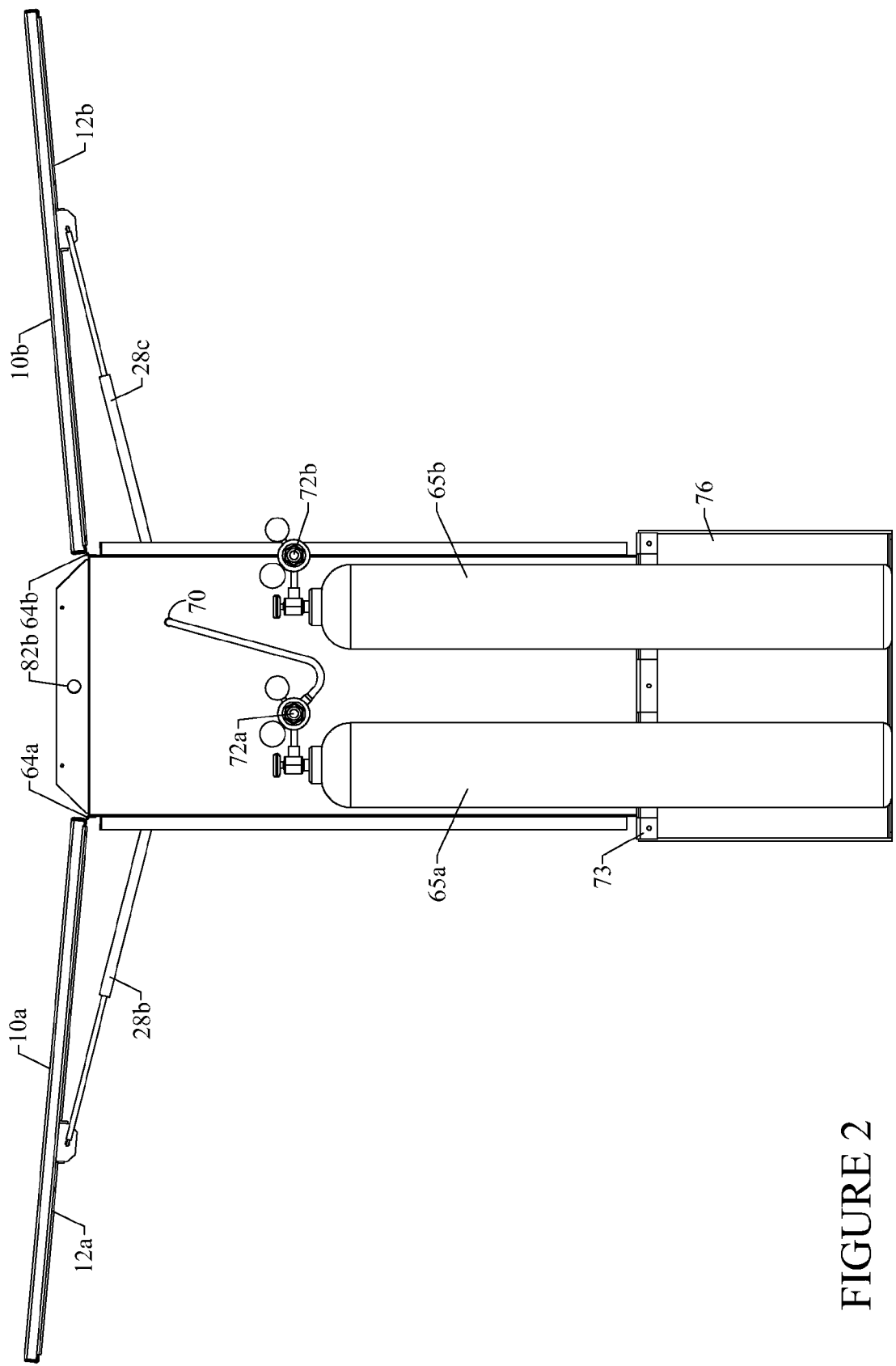
FIG. 2 illustrates a side view of an enclosure containing a gas chromatograph in accordance with one embodiment of the present invention.

Turning now to FIG. 2, a side view of the gas chromatograph enclosure 8, which shows two movable doors 10a, 10b, which can be pivotally mounted to the body 9 by hinges 64a, 64b. Pneumatic shocks 28b, 28c are illustrated holding each movable door 10a, 10b in an open position.

In an embodiment pneumatic shocks 28a, 28d are not visible in FIG. 2, but can be located opposite pneumatic shocks 28b, 28c, while in another embodiment each door can require a single pneumatic shock or multiple pneumatic shocks can be used. Seals 12a, 12b can be seen on the inner surface of the movable doors 10a, 10b for forming a sealing engagement between movable doors 10a, 10b, and the body 9. The seals 12a, 12b can prevent rain, dirt and other elements from reaching the interior of the body 9.

Purge gas tanks 65a, 65b are shown with purge gas regulators 72a, 72b on the side of the body held in place with a tank fastening system 73. The tank fastening system 73 can be secured to the pedestal 76, but can also be secured to the body 9. Purge gas conduit port 70 can be seen on the side of the body 9. Lifting eye 82b is seen in a flange which can be welded to the top of the body 9. A second flange on the opposite side of the body cannot be seen in this Figure, but can provide a balanced system for lifting and moving the gas chromatograph enclosure 8.

Figure 3:
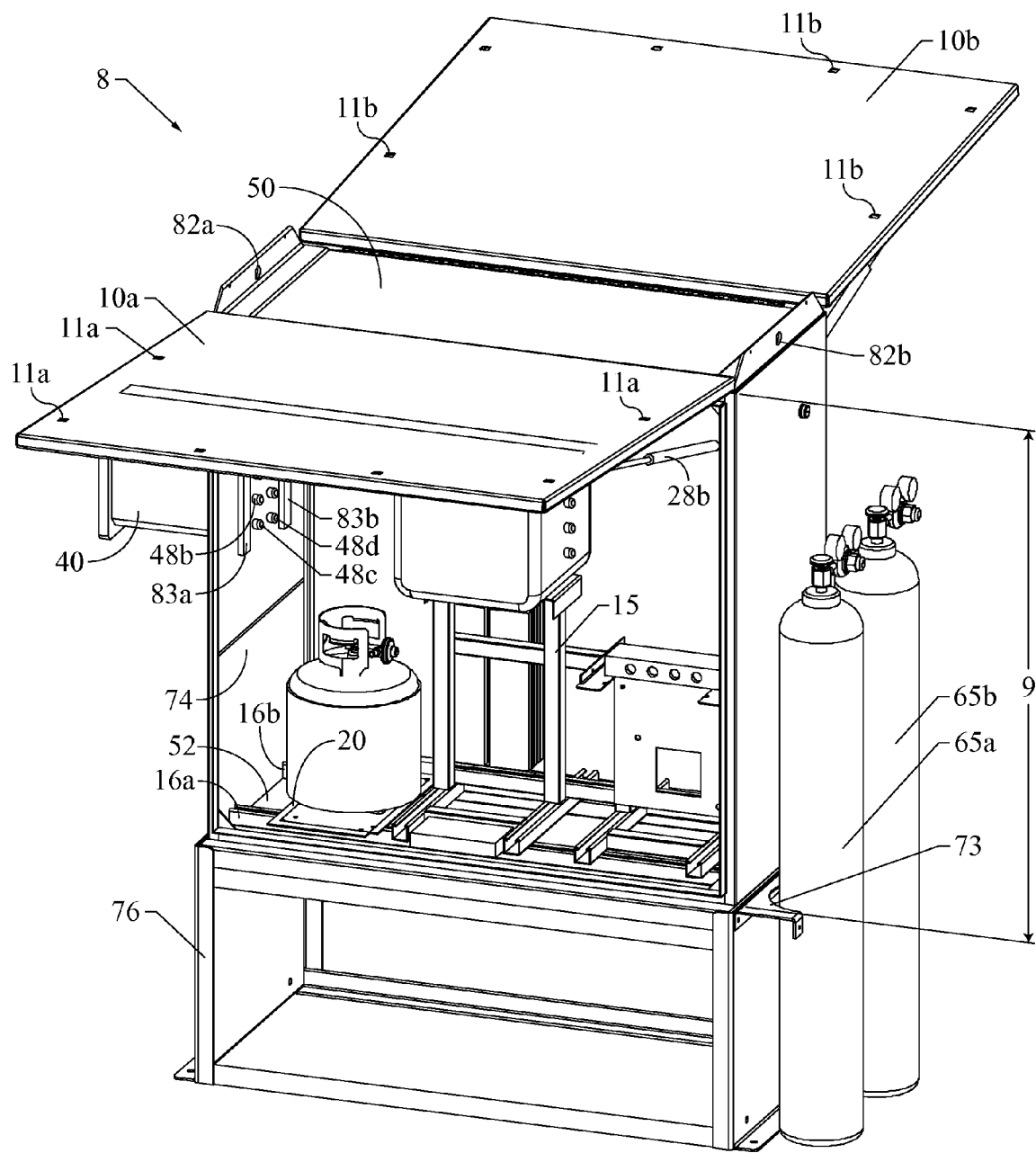
FIG. 3 illustrates a perspective view of an enclosure containing a gas chromatograph in accordance with one embodiment of the present invention.

FIG. 3 illustrates a perspective view of the gas chromatograph enclosure 8 including a body 9 supported on a pedestal 76. Each of the movable doors 10a, 10b are illustrated in the open position. Movable door 10a can have at least one fastener 11a, in additional embodiments, additional fasteners can be used. Movable door 10b can have at least one fastener 11b, in an additional embodiment, additional fasteners can be used.

The body 9 can also include supports 16a, 16b. The supports 16a, 16b can be constructed from steel or another rigid material. The support 16a can provide the body 9 with extra rigidity, helping prevent the body 9 from deforming even when the entire gas chromatograph enclosure 8 is lifted or moved. The supports 16a, 16b can also serve as a place for mounting the support assembly 15 and the calibration gas assembly 20.

The parallel stiff non-deformable bars 83a, 83b are illustrated opposite the explosion proof terminal box 40, and can be used for mounting the explosion proof terminal box 40 to the wall.

The gas chromatograph 14 can be supported by the support assembly 15 generally in the center of the body 9.

The lifting eyes 82a, 82b can be parallel to each other on opposite sides of the body. These lifting eyes 82a, 82b can provide a balanced means for lifting and moving the entire enclosure. In an embodiment, additional lifting eyes can be used.

FIG. 3 further illustrates purge gas sources 65a, 65b, which can be supported by the tank fastening system 73.

FIG. 4 illustrates a power source 68 used in conjunction with certain embodiments of the gas chromatograph enclosure 8. The power source 68 can be connected to a circuit breaker 42 and a terminal 44. The power source 68 can be located within or connected to the explosion proof terminal box 40. The explosion proof terminal box 40 can be electrically connected to the heating blanket (78).

FIG. 4 illustrates a power source 68 used in conjunction with certain embodiments of the gas chromatograph enclosure 8. The power source 68 can be connected to a circuit breaker 42 and a terminal 44. The power source 68 can be located within or connected to the explosion proof terminal box 40.

While these embodiments have been described with emphasis on the embodiments, it should be understood that within the scope of the appended claims, the embodiments might be practiced other than as specifically described herein.

What is claimed is:

1. A portable weather resistant gas chromatograph system with a gas chromatograph enclosure comprising:
   a. a body comprising a top, a bottom, and at least two walls, connected to each top and bottom, and further wherein each wall has an outer side and an inner side;
   b. at least one movable door mounted to the body;
   c. at least one movable door fastener for securing the at least one movable door to the body;
   d. at least one seal disposed on each movable door for providing a weather tight sealing engagement with the body;
   e. a gas chromatograph with a frame assembly secured to the bottom of the body wherein the gas chromatograph is adapted to receive sample gas, purge gas, and calibration gas during operation of the gas chromatograph;
   f. at least one exhaust gas line fluidly connected between the gas chromatograph and the body;
   g. an explosion proof terminal box mounted to an outer side of one of the walls, and wherein the explosion proof terminal box is in communication with the gas chromatograph through the wall and wherein the explosion proof terminal box comprises at least one circuit breaker and at least one terminal wherein the terminal can engage a power source;
   h. a conduit for providing communication between the explosion proof terminal box and the gas chromatograph;
   i. at least one armored power cable providing power between the explosion proof terminal box and the gas chromatograph;
   j. at least one purge gas conduit port penetrating one of the walls for receiving purge gas for the gas chromatograph from at least one purge gas source;
   k. a pedestal for maintaining the gas chromatograph enclosure above a surface; and
   l. at least one lifting eye connected to the body enabling lifting of the portable weather resistant gas chromatograph system without deforming the body.

2. The system of claim 1, wherein a support comprises at least two parallel stiff non-deformable bars secured to the inner side of the wall perpendicular to a plane of the bottom for supporting the explosion proof terminal box.

3. The system of claim 1, further comprising at least one heater within the body.

4. The system of claim 1, further comprising a calibration gas tank with calibration gas 23 in communication with the gas chromatograph.

5. The system of claim 4, further comprising at least one heating blanket disposed around the calibration gas tank and wherein the at least one heating blanket receives power from the explosion proof terminal box.

6. The system of claim 1, further comprising at least one tank fastening system removably mounted to an outer side of one of the walls.

7. The system of claim 1, further comprising insulation disposed on at least a portion of the inner sides of the walls.

8. The system of claim 1, further comprising a purge gas regulator fluidly connected between the at least one purge gas port and the at least one purge gas source for reducing pressure of purge gas prior to flowing the purge gas to the gas chromatograph.

9. The system of claim 1, wherein the at least one exhaust gas line can be selected from the group consisting of: a sample gas, a purge gas, an inert gas, and another gas.

10. The system of claim 1, wherein the conduit comprises a plurality of sealing fittings.

11. The system of claim 1, further comprising between one circuit breaker and six circuit breakers and between six terminals and twenty-four terminals in the explosion proof terminal box.

12. The system of claim 1, further comprising at least one hinge for connecting each movable door to the body.

13. The system of claim 1, further comprising a manifold in fluid communication with the at least one exhaust gas line for venting exhaust gas from the body.

14. The system of claim 1, further comprising a foldable tray disposed adjacent to the frame assembly for supporting a computer.

15. The system of claim 1, further comprising at least one pressure relief valve disposed in at least one of the walls.

16. The system of claim 1, further comprising at least one pneumatic shock end secured on an inner side of one of the walls of the body and the other end secured on the at least one movable door.

17. The system of claim 16, further comprising at least one channel bracket disposed between the at least one pneumatic shock end and one of the walls.

18. The system of claim 1, further comprising at least one support secured to the frame assembly between the inner sides of the walls.

19. The system of claim 1, wherein the pedestal further comprises at least one pedestal flange for mounting the gas chromatograph system.

* * * * *